United States Patent [19]

Friedman et al.

[11] Patent Number: 5,100,323
[45] Date of Patent: Mar. 31, 1992

[54] DENTAL IMPLANT

[75] Inventors: Kurt E. Friedman, Plantation; James E. Davis, Fort Lauderdale, both of Fla.

[73] Assignee: Impla-Med Incorporated, Sunrise, Fla.

[21] Appl. No.: 577,787

[22] Filed: Sep. 5, 1990

[51] Int. Cl.$^5$ ............................................. A61C 8/00
[52] U.S. Cl. .................................................. 433/173
[58] Field of Search ............... 433/173, 174, 175, 176, 433/201.1

[56] References Cited

U.S. PATENT DOCUMENTS

| | | | |
|---|---|---|---|
| 3,022,783 | 2/1962 | Tucker, Jr. | 128/1 |
| 3,499,222 | 3/1970 | Linkow et al. | 433/174 |
| 3,605,123 | 9/0971 | Hahn | 3/1 |
| 3,767,437 | 10/1973 | Cruz, Jr. | 106/161 |
| 3,919,723 | 11/1975 | Heimke | 3/1.9 |
| 3,979,828 | 9/1976 | Taylor | 433/175 |
| 3,986,212 | 10/1976 | Sauer | 3/1.91 |
| 3,987,499 | 10/1976 | Scharbach | 3/1.91 |
| 4,051,598 | 10/1977 | Sneer | 433/173 |
| 4,180,910 | 1/1980 | Straumann | 433/173 |
| 4,261,350 | 4/1981 | Branemark et al. | 128/92 |
| 4,431,416 | 2/1984 | Niznick | 433/174 |
| 4,459,111 | 7/1984 | Valen | 433/176 |
| 4,468,200 | 8/1984 | Munch | 433/174 |
| 4,486,178 | 12/1984 | Schulte | 433/173 |
| 4,492,577 | 1/1985 | Farris | 433/201 |
| 4,521,192 | 6/1985 | Linkow | 433/173 |
| 4,522,596 | 6/1985 | Ashkinazy | 433/173 |
| 4,531,915 | 7/1985 | Tatum, Jr. | 433/173 |
| 4,531,916 | 7/1985 | Scantlebury | 433/173 |
| 4,531,917 | 7/1985 | Linkow et al. | 433/176 |
| 4,538,304 | 9/1985 | Grafelmann | 623/16 |
| 4,552,532 | 11/1985 | Mozsary | 433/173 |
| 4,560,353 | 12/1985 | Schulte et al. | 433/173 |
| 4,573,922 | 3/1986 | Bello | 433/176 |
| 4,599,085 | 7/1986 | Riess et al. | 433/201.1 |
| 4,600,388 | 7/1986 | Linkow | 433/176 |
| 4,600,391 | 7/1986 | Jacob | 433/220 |
| 4,626,214 | 12/1986 | Artal | 433/174 |
| 4,657,510 | 4/1987 | Gittleman | 433/173 |
| 4,661,066 | 4/1987 | Linkow et al. | 433/176 |

(List continued on next page.)

FOREIGN PATENT DOCUMENTS 2313678 3/1973 Fed. Rep. of Germany .
2289160 5/1976 France .
834256 5/1960 United Kingdom .

Primary Examiner—John J. Wilson
Attorney, Agent, or Firm—David P. Gordon

[57] ABSTRACT

A dental implant for supporting and positioning an artificial tooth or other prosthetic device in the mouth, and preventing its rotation is provided. The dental implant is adapted to be installed in a pre-drilled bore in the bone of the maxilla or mandible and is eseointegrated into the bone. The dental implant has a generally cylindrical body with a first end implanted in the bone and second end including an annular base. The cylindrical body also includes a threaded bore extending from the second end into the cylindrical body along the longitudinal axis of the cylindrical body. A hexagonal shaped protrusion, when viewed along the bore of the cylinder, is integrally attached to and extends away from the annular base. The central bore of the cylinder extends concentrically through both the annular base and the hexagonal protrusion. The hexagonal protrusion will mate with a corresponding shaped female recess in an abutment which supports and positions an artificial tooth or other prosthetic device above the gum material located above the bone. The abutment rests on both the annular base and the hexagonal projection. This mating relation prevents the abutment from rotating around hexagonal projection and thereby maintains the orientation of the abutment and corresponding artificial tooth or prosthetic device within the mouth. Although a hexagonal shaped protrusion is used in the preferred embodiment, any shape protrusion and corresponding shaped female recess which, when in mating contact, prevents the abutment form rotating around the male projection is within the scope of the invention.

21 Claims, 2 Drawing Sheets

U.S. PATENT DOCUMENTS

| | | | |
|---|---|---|---|
| 4,668,191 | 5/1987 | Plischka | 433/174 |
| 4,671,768 | 6/1987 | Ton | 433/174 |
| 4,693,686 | 9/1987 | Sendax | 433/173 |
| 4,702,697 | 10/1987 | Linkow | 433/173 |
| 4,713,003 | 12/1987 | Symington et al. | 433/173 |
| 4,713,004 | 12/1987 | Linkow et al. | 433/174 |
| 4,744,755 | 5/1988 | Ross | 433/173 |
| 4,758,160 | 7/1988 | Ismail | 433/173 |
| 4,762,492 | 9/1988 | Nagai | 433/174 |
| 4,768,956 | 9/1988 | Kurpis | 433/173 |
| 4,772,203 | 9/1988 | Scheunemann | 433/173 |
| 4,772,204 | 9/1988 | Saderberg | 433/174 |
| 4,780,080 | 10/1988 | Haris | 433/173 |
| 4,781,591 | 11/1988 | Allen | 433/174 |
| 4,790,753 | 12/1988 | Fradera | 433/174 |
| 4,799,886 | 1/1989 | Wimmer | 433/176 |
| 4,802,847 | 2/1989 | Komatsu | 433/176 |
| 4,812,120 | 3/1989 | Flanagan et al. | 433/173 |
| 4,818,559 | 4/1989 | Hama et al. | 427/2 |
| 4,850,870 | 7/1989 | Lazzara et al. | 433/174 |
| 4,854,872 | 8/1989 | Detsch | 433/173 |
| 4,854,875 | 8/1989 | Linden | 433/173 |
| 4,955,811 | 7/1990 | Lazzara et al. | 433/173 |
| 4,960,381 | 10/1990 | Niznick | 433/174 |

DENTAL IMPLANT

BACKGROUND OF THE INVENTION

1. Field of the Invention

This invention relates generally to dental implants and specifically to a cylindrical endosseous implant having an external engagement cap for locking engagement with an artificial dental appliance or prosthetic component.

2. Description of Prior Art

Endosseous implants are of basically three different types: blades, screws, and cylinders. Screws and cylinders both require that a hole be drilled into the jawbone. In the case of screws, the hole is then either tapped to accept a threaded screw implant or a self-tapping screw implant is threaded thereunto. The top of both these screw fixtures is typically provided with a hexagonal male projection adapted to mate with a correspondingly shaped relief provided in a screwing tool. The primary purpose for the hexagonal male projection is to engage a tool used to drive the implant into the bone and, to support prosthetic components thereon. An additional benefit of the male projections is that they may mate with corresponding female apertures on the prosthetic components to prevent the prosthetic components from rotating around the screw. In this way, the prosthetic component is locked in position above the screw.

A representative example of a screw-type implant is disclosed in U.S. Pat. No. 4,713,004 to Linkow et al. Linkow discloses an implant having screw threads along its elongate body portion and a hex projection connected at its upper end adapted to be engaged by a screwing tool.

A cylinder-type implant having a threaded central bore is installed by first drilling a hole into the bone. The inner diameter of this hole is equal to or slightly less than the cylinder to be installed. The cylinder implant is then introduced into the hole and forcibly tapped into place with a small mallet. A cover screw is threaded into the open bore of the cylinder. The cover screw protects the top of the cylinder. In the ideal case, there is an interference fit between the cylinder and the hole. The top of the cylinder-type implant is not provided with a hexagonal member because a threading tool is not necessary to install the cylinder-type implant as with a screw implant. The choice of whether to use a screw or a cylinder is strictly up to the surgeon and dependent on the quality of bone at the implant site.

The cylinder-type implant is greatly preferred and, in fact, must be used in lieu of the screw-type implant where the bone matter of the mandible or maxilla is soft or scarce. Because the bone matter of the maxilla is typically softer than bone matter of the mandible, cylinders are almost exclusively used in the maxilla. In addition, because the bone matter of older patients, in both the maxilla and mandible, is softer than in ordinary patients, cylinders are preferred in both the maxilla and mandible of older clients.

The cylinder implant is installed by pushing the body portion thereof straight into a hole drilled into the bone. The top of the cylinder implant is located at about the surface of the bone and includes a threaded bore extending into the cylinder body. This threaded bore receives anchoring fasteners such as screws to hold prosthetic components in place above the cylinder.

An abutment, which is typically a hollow cylinder with a central bore is placed on top of the cylinder through the gum material located above the bone to provide a platform for a replacement tooth or artificial dental appliance. The central bore of the abutment is colineal with the central bore of the cylinder when the abutment is placed on top of the cylinder. The replacement tooth or appliance also has an aperture colineal with the bore of the cylinder and the abutment. Screws extending through the prosthetic device and the abutment are used to secure the abutment and the prosthetic device in place.

Heretofore, however, the surgeon utilizing the cylinder-type implant has not had the benefit of the locking hexagonal or otherwise shaped male projection member mating with a corresponding aperture in the abutment in order to obtain a secure and relatively permanent fit and orientation between the cylinder and the dental replacement structure.

An additional problem for most prosthodontists and restorative dentists working with cylinder implants has been that the prosthetic components available for screw type implants are much more numerous and versatile and allow for more options as the need arises. None of the cylinder-type dental implants known in the prior art are provided with a hexagonal or otherwise shaped projection onto which a replacement dental structure may be lockingly engaged.

SUMMARY OF THE INVENTION

An endesseous implant comprising a rigid cylindrically shaped body having a hemispherical shaped base, and a hexagonally shaped male projection cap integrally connected to the cylinder implant body opposite the hemispherical base is disclosed. The cylinder body is preferably comprised of commercially pure titanium and is adapted to be installed as are conventional cylinder-type implants. The internally threaded bore of the implant cylinder matches the internal threads of the screw-type implant as do the standard range of dimensions of the hexagonal member. The cylinder portion of the new implant matches the standard cylinder-type implant yet has an upper, or receptor, member that accepts the variety of prosthetic components heretofore used only with screw-type implants. The cylinder body may also include recesses extending into or through the cylinder body to enhance the oseointegration of the cylinder body with the surrounding bone.

The cylinder body is preferably coated first with a coating of titanium plasma and then with a coating of hydroxylapatite to enhance the oseointegration process by increasing the surface area of the cylinder and improving the bond strength between the bore and the cylinder. Although this is the preferred coating scheme, other coating schemes of these materials, either individually or in combination, as well as other materials that enhance the oseointegration process may be used.

It is an object of this invention to provide a cylinder-type implant that combines the advantages of a cylinder implant with the variety of prosthetic devices available with screw implants.

It is another object of this invention to provide an apparatus which overcomes the aforementioned inadequacies of the prior art devices and provides an improvement which is a significant contribution to the advancement of the dental implant art.

Another object of this invention is to provide a dental implant which is rigidly securable within the socket or alveolar of an extracted tooth or prepared opening to provide a suitable foundation for a prosthesis such as a crown or replacement tooth.

Another object of this invention is to provide a dental implant which does not threadably engage the socket or alveolar of the extracted tooth or other opening but rather is inserted therein, and which further comprises a male projection member connected integrally to its upper end adapted to mate with a corresponding recess disposed within an artificial dental appliance to resist turning of said artificial dental appliance relative to said implant.

In accordance with these and other objects which will be apparent hereinafter, the instant invention will now be described with particular reference to the accompanying drawings.

DETAILED DESCRIPTION OF THE INVENTION

Figure 1:
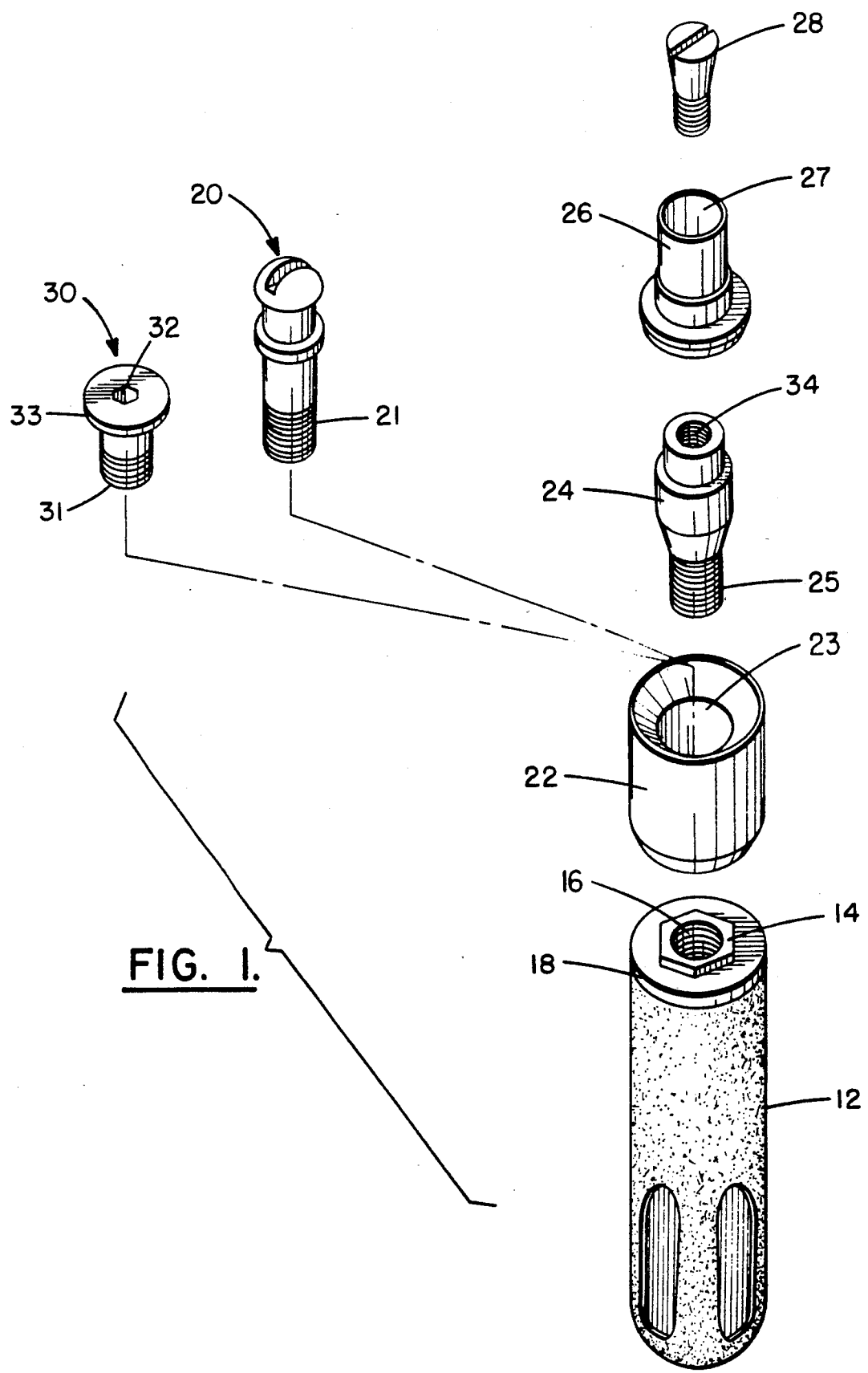
FIG. 1 is an exploded view of the implant and associated parts.

The cylinder 12 (FIG. 1) is shown having an annular base 18 integrally attached at one end and a hemispherical-shaped end opposite the annular base 18. Annular base 18 has a planar top surface opposite the hemispherical-shaped end of cylinder 12. Ideally, the diameter of cylinder 12 and annular base 18 varies from 3.3-4.0 milimeters, while the length of cylinder 12 varies from 8-15 milimeter. However, the sizes given are merely exemplary and are not for limitation.

Figure 2:
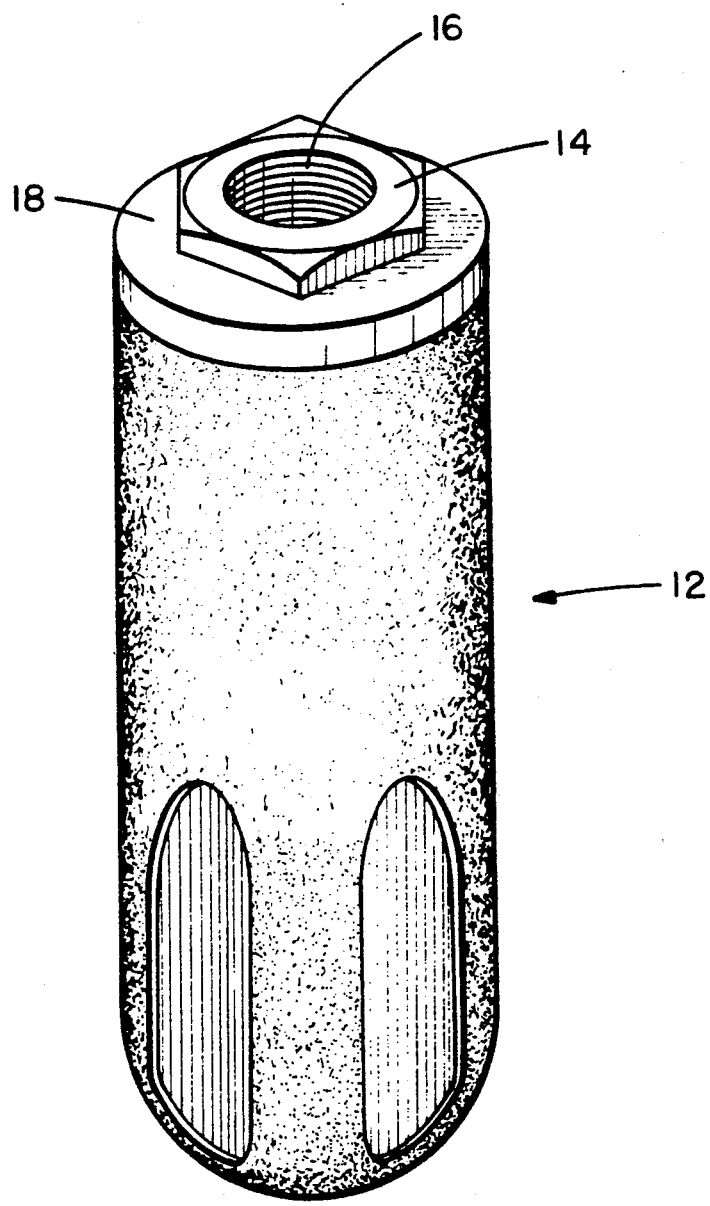
FIG. 2 is a perspective view of the cylinder implant including the male projection integrally connected to the top of the cylinder body.

Attached to the top of base 18 is a hexagonal projection 14 (FIG. 2) concentrically arranged around a threaded bore 16 which extends through hexagonal projection 14 and annular base 18 into cylinder 12. Hexagonal projection 14 is larger in diameter than bore 16 so that bore extends through hexagonal projection 14. Hexagonal projection 14 is rigidly attached to and extends away from annular base 18. In addition, hexagonal projection 14 has a planar top surface parallel to the top surface of annular base 18. The sides of hexagonal projection 14, corresponding to the hexagonal shape of hexagonal projection 14 when viewed along the axis of the threaded bore 16, extend downward from the top surface of hexagonal projection to the top surface of annular base 18 in a generally perpendicular direction to both top surfaces.

A generally cylindrically-shaped abutment 22 having a central bore 23 extending through the abutment 22 along its longitudinal axis is provided having a female hexagonal recess (not shown) concentric with the central bore 23 and corresponding in shape and size to the male hexagonal projection 14. Just as the male hexagonal projection 14 is larger in diameter than bore 16, female hexagonal recess (not shown) is larger in diameter than bore 23 extending through abutment 22. When abutment 22 is placed in contact with male hexagonal projection 14 and base 18, abutment 22 will be securely held in position relative to cylinder 12 by the mating interaction of male hexagonal projection 14 and the corresponding female hexagonal recess. In this position, bore 16 of cylinder 12 and bore 23 extending through abutment 22 will be colineal. Bore 23 is non-threaded and extends entirely through abutment 22.

Although a hexagonal shaped projection 14 and corresponding shaped female recess has been described which prevents abutment 22 from rotating around cylinder 12, any shaped male projection and corresponding shaped female recess having the property that when both are in a mating configuration, rotation of one causes the corresponding rotation of the other, is within the scope of the invention. Examples of such shapes for the male projection, given as examples and not for limitation, are square, rectangle, star, triangle, oval and free-formed.

Temporary installation piece 20 is provided with external threads 21 which intermesh with the internal threads of bore 16 of cylinder 12 Temporary installation piece 20 assists in the placement of cylinder 12 as is described hereafter. In addition, a cover screw 30 is provided to seal bore 16 after cylinder 12 has been placed in the hole drilled in the bone while the bio-integration process occurs.

Abutment screw 24 with external threads 25 corresponding to the threads of bore 16 extends through the non-threaded bore 23 of abutment 22 and intermeshes with the threads of bore 16. A threaded bore 34 extends into the top of abutment screw 24 opposite threads 25. Abutment screw 24 is tightened into bore 16 by rotating abutment screw 24 so that abutment 22, including the female hexagonal recess (not shown), is drawn into secure contact with the male hexagonal projection 14 and the base 18 of cylinder 12.

Cylinder 12, hexagonal projection 14, base 18, cover screw 20, abutment 22 and abutment screw 24 are all preferably made of commercially pure titanium. In addition, cylinder 12 is covered with a coating of hydroxylapatite or titanium plasma which aids in the bio-integration of the cylinder 12 with the surrounding bone.

An artificial tooth or other prosthetic device is placed around a gold cylinder 26 having a non-threaded bore 27. A gold screw 28 extends through non-threaded bore 27 into the threaded bore 34 at the top of abutment screw 24. Gold screw 28, when screwed into threaded bore 34, securely and frictionally holds gold cylinder 26, and the corresponding artificial tooth or prosthetic device, in place relative to the top of abutment 22. Abutment 22 is held in place relative to cylinder 12, and therefore relative to the bone, and is prevented from rotating around cylinder 12 by the interaction of male hexagonal projection 14 with the female hexagonal recess (not shown) in abutment 22.

To install the implant device, a hole is drilled into the bone which is the same as or slightly smaller in diameter than the diameter of cylinder 12. Temporary installation piece 20 is then threaded in the bore 16 by interaction of threads 21 on temporary installation piece 20 with the threads of bore 16, thereby providing a cap or protective covering for hexagonal projection 14 and bore 16. Cylinder 12 and temporary installation piece 20 are then placed in the hole drilled into the bone and are gently tapped into place by a small mallet making contact with temporary installation piece 20. Cylinder 12 is driven into the hole in the bone until the top of hexagonal projection 14 is flush with the top of the bone. Temporary installation piece 20 is then removed exposing bore 16 of cylinder 12.

Cover screw 30 having external threads 31, a hexagonal recess 32 opposite threads 31, and a body 33 with a planar lower surface, is then screwed into bore 16 until body 33 contacts the top of hexagonal projection 14, thereby providing a seal between body 33 and the top of bore 16 at hexagonal projection 14. Hexagonal recess 32 allows a hexagonal tool to be inserted therein to rotate cap implant 30 in threading relation in bore 16. Alternately, hexagonal recess 32 may be replaced by a slot running across the top surface of body 33 allowing cover screw 30 to be rotated by the insertion and rotation of a blade-type tool. After cover screw 30 has sealingly contacted hexagonal projection 14, cylinder 12 is left in the bone for bio-integration to take place, thereby securing cylinder 12 in the bone.

After a sufficient amount of time has transpired to allow cylinder 12 to be bio-integrated into the bone mass, cover screw 30 is removed from cylinder 12 by rotating cap implant 30 through hexagonal recess 32 or through the slot across the top surface of body 33, thereby exposing bore 16. At this time abutment 22, with female hexagonal recess (not shown) is placed in contact with male hexagonal projection 14. The interaction of male hexagonal projection 14 with female hexagonal recess (not shown) secures abutment 22 from rotating around male hexagonal projection 14. This interaction securely positions abutment 22 with respect to cylinder 12 and prevents rotation around cylinder 12. Abutment 22 provides a base for the subsequent attachment of gold cylinder 26 and the corresponding artificial tooth or prosthetic device, above the gum material which surrounds the bone to which the cylinder 12 is implanted.

Abutment screw 24 is placed through the non-threaded bore 23 of abutment 22 so that threads 25 of the abutment screw 24 come into functional contact with the threads of bore 16. As abutment screw 24 is screwed into bore 16, abutment 22 is securely held in place by the interaction of male hexagonal projection 14 and female hexagonal recess (not shown).

Gold cylinder 26, with its corresponding artificial tooth or prosthetic device, is then placed on the top of abutment screw 24 where it also contacts the top of abutment 22. Gold screw 28 is placed through non-threaded bore 27 of gold cylinder 2 and is securely threaded into threaded bore 34 of abutment screw 24. Gold screw 28 frictionally holds gold cylinder 26, and therefore the corresponding artificial tooth or prosthetic device, in place on the top of abutment 22 and abutment screw 24.

Abutment screw 24 is prevented from rotating by its frictional interaction with abutment 22 which is in turn prevented from rotating by the interaction of male hexagonal projection 14 and female hexagonal recess (not shown). Because abutment 22 and abutment screw 24 are prevented from rotating, gold cylinder 26 is also prevented from rotating by the frictional interaction of gold cylinder 26 with abutment 22 and abutment screw 24. In this way, the artificial tooth or other prosthetic device attached to gold cylinder 26 is prevented from rotating around cylinder 12 in a way which has not heretofore been available with such cylinders.

Although the dental implant has been described in connection with specific embodiments, it is to be clearly understood that this description is given by means of example and not for limitation. It is clear that changes and modifications to the embodiments described herein can be made within the scope of the invention. Further, it is recognized that obvious changes and modifications will occur to one skilled in the art.

What I claim is:

1. A dental implant adapted to be inserted by pushing or tapping into a pre-drilled bore in the bone of the maxilla or mandible, said dental implant being supported and anchored within said pre-drilled bore by the in-growth of bone material in and around said dental implant, said dental implant for supporting and positioning an artificial tooth or other prosthetic device in the mouth, comprising:

a) a generally cylindrical body having no external threads, and having a first end for implanting in the maxilla or mandible bone, and a second end, said cylindrical body including a threaded central bore extending from said second end toward said first end, said second end including an integral annular base concentric with said central bore; and, b) a hexagonal shaped protrusion attached to and extending away from said base of said cylindrical body, said hexagonal shaped protrusion concentric to said central bore of said cylindrical body, said hexagonal shaped protrusion being smaller in concentric diameter than said base so that a portion of said base extends away from said hexagonal shaped protrusion,;

whereby an annular abutment, having a first end for supporting said artificial tooth or prosthetic device and a second end having a recess corresponding in shape to said hexagonal shaped protrusion, when placed in contact with said base so that said hexagonal shaped protrusion is in contact with said recess, will be frictionally prevented from rotating around said central bore by the interaction of said hexagonal shaped protrusion with said recess, said threaded central bore of said cylindrical body for receiving a temporary installation piece to aid in insertion of said cylindrical body in said bone and for receiving an abutment screw through said annular abutment whereby said abutment, by the tightening of said abutment screw into said central bore, is brought into secure contact with said base and whereby said hexagonal shaped protrusion and said recess, by tightening said abutment screw, are brought into secure frictional contact thereby preventing the rotation of said abutment around the central axis of said cylindrical body.

2. The dental implant of claim 1 wherein said cylindrical body, said hexagonal shaped protrusion, said abutment, said cover screw and said abutment screw are manufactured substantially of titanium.

3. The dental implant of claim 1 wherein said cylindrical body is coated with a coating of hydroxylapatite or titanium plasma to enhance endosseous integration of said cylindrical body in said bone.

4. The dental implant of claim 1 wherein the diameter of said annular base is equal to the diameter of said cylindrical body.

5. A dental implant adapted to be inserted by pushing or tapping into a pre-drilled bore in the bone of the maxilla or mandible, said dental implant being supported and anchored within said pre-drilled bore by the in-growth of bone material in and around said dental implant, said dental implant for supporting and positioning an artificial tooth or other prosthetic device in the mouth, comprising:

a) a generally cylindrical body having no external threads, and having a first end for implanting in the maxilla or mandible bone, and a second end, said cylindrical body including a threaded central bore extending from said second end toward said first end, said second end including an integral annular base concentric with said central bore;

b) a hexagonal shaped protrusion attached to and extending away from said base of said cylindrical body, said hexagonal shaped protrusion concentric to said central bore of said cylindrical body, said hexagonal shaped protrusion smaller in concentric diameter than said base so that a portion of said base extends away from said hexagonal shaped protrusion; and c) an annular abutment, having a first end for supporting said artificial tooth or prosthetic device and a second end having a recess corresponding in shape to said hexagonal shaped protrusion, so that said abutment, when placed in contact with said base so that said hexagonal shaped protrusion is in contact with said recess, will be frictionally prevented from rotating around said central bore by the interaction of said hexagonal shaped protrusion with said recess, said threaded central bore of said cylindrical body for receiving a temporary installation piece in the form of a cover screw to aid in insertion of said cylindrical body in said bone and for receiving an abutment screw through said annular abutment whereby said abutment, by the tightening of said abutment screw into said central bore, is brought into secure contact with said base and whereby said hexagonal shaped protrusion and said recess, by tightening said abutment screw, are brought into secure frictional contact thereby preventing the rotation of said abutment around the central axis of said cylindrical body.

6. The dental implant of claim 5 wherein said cylindrical body, said hexagonal shaped protrusion, said abutment, said cover screw and said abutment screw are manufactured substantially of titanium.

7. The dental implant of claim 5 wherein said cylindrical body is coated with a coating of hydroxylapatite or titanium plasma to enhance endosseous integration of said cylindrical body in said bone.

8. The dental implant of claim 5 wherein the diameter of said annular base is equal to the diameter of said cylindrical body.

9. A dental implant adapted to be inserted by pushing or tapping into a pre-drilled bore in the bone of the maxilla or mandible, said dental implant being supported and anchored within said pre-drilled bore by the in-growth of bone material in and around said dental implant, said dental implant for supporting and positioning an artificial tooth or other prosthetic device in the mouth, comprising:

a) a cylindrical smooth surfaced body having a first end for implanting in the maxilla or mandible bone, and a second end, said cylindrical body including a threaded central bore extending from said second end toward said first end, said second end including an integral annular base equal in diameter to the diameter of said cylindrical body; and, b) a hexagonal shaped protrusion attached to and extending away from said base of said cylindrical body, said hexagonal shaped protrusion concentric to said central bore of said cylindrical body, said hexagonal shaped protrusion smaller in concentric diameter than said base so that a portion of said base extends away from said hexagonal shaped protrusion; and whereby an annular abutment, having a first end for supporting said artificial tooth or prosthetic device and a second end having a recess corresponding in shape to said hexagonal shaped protrusion, when placed in contact with said base so that said hexagonal shaped protrusion is in contact with said recess, will be frictionally prevented from rotating around said central bore by the interaction of said hexagonal shaped protrusion with said recess, said threaded central bore of said cylindrical body for receiving a temporary installation piece in the form of a cover screw to aid in placement of said cylindrical body in said bone and for receiving an abutment screw through said annular abutment whereby said abutment, by the tightening of said abutment screw into said central bore, is brought into secure contact with said base and whereby said hexagonal shaped protrusion and said recess, by tightening said abutment screw, are brought into secure frictional contact thereby preventing the rotation of said abutment around the central axis of said cylindrical body.

10. The dental implant of claim 9 wherein said cylindrical body, said hexagonal shaped protrusion, said abutment, said cover screw and said abutment screw are manufactured substantially of titanium.

11. The dental implant of claim 9 wherein said cylindrical body is coated with a coating of hydroxylapatite or titanium plasma to enhance endosseous integration of said cylindrical body in said bone.

12. A dental implant adapted to be inserted by pushing or tapping into a pre-drilled bore in the bone of the maxilla or mandible, said dental implant for supporting and positioning an artificial tooth or other prosthetic device in the mouth, comprising:

a) a generally cylindrical body having no external threads, and having a first end for implanting in the maxilla or mandible bone, and a second end, said cylindrical body including a threaded central bore extending from said second end toward said first end, said second end including an integral annular base concentric with said central bore; and b) a hexagonal shaped protrusion attached to and extending away from said base of said cylindrical body, said hexagonal shaped protrusion concentric to said central bore of said cylindrical body, said hexagonal shaped protrusion being smaller in concentric diameter than said base so that a portion of said base extends away from said hexagonal shaped protrusion.

13. A dental implant according to claim 12, in conjunction with an annular abutment having a smooth axial bore and a first end for supporting said artificial tooth or prosthetic device and a second end having a recess communicating with said axial bore and corresponding in shape to said hexagonal shaped protrusion, so that said abutment, when placed in contact with said base so that said hexagonal shaped protrusion is in contact with said recess, will be frictionally prevented from rotating around said central bore by the interaction of said hexagonal shaped protrusion with said recess.

14. The combination of claim 13 in conjunction with an abutment screw having a threaded portion configured to pass freely through said axial bore of said annular abutment and having external threads for threadably engaging said central bore and having an internally threaded axial bore.

15. The combination of claim 14 in conjunction with a cylinder member having a smooth axial bore and being adapted to be seated on said annular abutment for supporting a prosthetic device.

16. The combination of claim 15 in conjunction with a holding screw member having a threaded portion configured to pass freely through said axial bore of said cylinder member for threadably engaging said internally threaded axial bore of said abutment screw to secure said cylinder member to said abutment.

17. A dental implant adapted to be inserted by pushing or tapping into a pre-drilled bore in the bone of the maxilla or mandible, said dental implant for supporting and positioning an artificial tooth or other prosthetic device in the mouth, comprising:
   a) a generally cylindrical smooth surfaced body having a first end for implanting in the maxilla or mandible bone, and a second end, said generally cylindrical smooth surfaced body including a threaded central bore extending from said second end toward said first end, said second end including an integral annular base concentric with said central bore; and
   b) a hexagonal shaped protrusion attached to and extending away from said base of said generally cylindrical smooth surfaced body, said hexagonal shaped protrusion concentric to said central bore of said generally cylindrical smooth surfaced body, said hexagonal shaped protrusion being smaller in concentric diameter than said base so that a portion of said base extends away from said hexagonal shaped protrusion.

18. A dental implant according to claim 17, in conjunction with an annular abutment having a smooth axial bore and a first end for supporting said artificial tooth or prosthetic device and a second end having a recess communicating with said axial bore and corresponding in shape to said hexagonal shaped protrusion, so that said abutment, when placed in contact with said base so that said hexagonal shaped protrusion is in contact with said recess, will be frictionally prevented from rotating around said central bore by the interaction of said hexagonal shaped protrusion with said recess.

19. The combination of claim 18 in conjunction with an abutment screw having a threaded portion configured to pass freely through said axial bore of said annular abutment and having external threads for threadably engaging said central bore and having an internally threaded axial bore.

20. The combination of claim 19 in conjunction with a cylinder member having a smooth axial bore and being adapted to be seated on said annular abutment for supporting a prosthetic device.

21. The combination of claim 20 in conjunction with a holding screw member having a threaded portion configured to pass freely through said axial bore of said cylinder member for threadably engaging said internally threaded axial bore of said abutment screw to secure said cylinder member to said abutment.

* * * * *